United States Patent [19]

Tomita et al.

[11] Patent Number: 4,593,097

[45] Date of Patent: Jun. 3, 1986

[54] PHENAZINE CARBOXYLIC ACID DERIVATIVES AND A PROCESS FOR PRODUCTION THEREOF

[75] Inventors: Fusao Tomita; Keiichi Takahashi, both of Machida; Isao Kawamoto, Hiratsuka; Kozo Asano, Machida; Makoto Morimoto, Shizuoka; Tadashi Ashizawa, Numazu; Kazuhisa Fujimoto, Shizuoka, all of Japan

[73] Assignee: Kyowa Hakko Kogyo Co., Ltd., Tokyo, Japan

[21] Appl. No.: 575,294

[22] Filed: Jan. 30, 1984

[30] Foreign Application Priority Data

Jan. 28, 1983 [JP] Japan .................................. 58-12383

[51] Int. Cl.[4] .................. C07D 241/46; C12P 17/12
[52] U.S. Cl. ...................... 544/347; 435/122
[58] Field of Search ......................... 544/347

[56] References Cited

U.S. PATENT DOCUMENTS 4,400,510  8/1983  Michel ........................... 544/347

OTHER PUBLICATIONS

Umezawa et al, *Chem. Abs.*, 92, 213541p (1980).

*Primary Examiner*—Mark L. Berch
*Attorney, Agent, or Firm*—Antonelli, Terry & Wands

[57] ABSTRACT

Phenazine compounds represented by the formula:

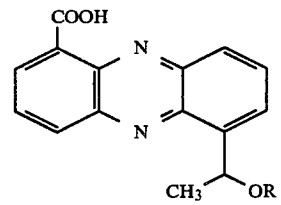

wherein R is a hydrogen atom, an unsubstituted or substituted lower alkanoyl group, or an unsubstituted or substituted arylcarbonyl group have antibacterial and anti-tumor activities.

Some of these compounds are produced by incubation of a microorganism.

5 Claims, 8 Drawing Figures

PHENAZINE CARBOXYLIC ACID DERIVATIVES AND A PROCESS FOR PRODUCTION THEREOF

BACKGROUND OF THE INVENTION

The present invention relates to novel phenazine compounds. More particularly, the present invention relates to novel phenazines represented by general formula (I):

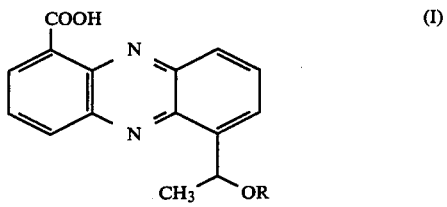

wherein R represents a hydrogen atom, an unsubstituted or substituted lower alkanoyl group, or an unsubstituted or substituted arylcarbonyl group (hereinafter referred to as Compound (I)), a process for the production thereof and a pharmaceutical composition containing the compound.

Compounds having excellent pharmacological activities are always in demand and for this purpose, substances produced by a microorganism separated from the soil (hereinafter referred to as DO-86 strain) have been investigated. As a result, it has been found that compounds represented by general formula (I-a):

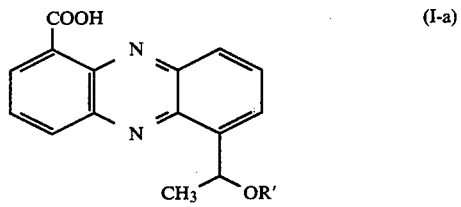

wherein R' represents a hydrogen atom (hereinafter the compound is referred to as DC-86-Y) or COCH$_2$OH (hereinafter the compound is referred to as DC-86-M) are produced and these compounds possess antibacterial and anti-tumor activities. As a result of further investigations, it has been found that phenazine compounds having more excellent antibacterial and anti-tumor activities can be prepared from DC-86-Y.

DETAILED DESCRIPTION OF THE INVENTION

The alkanoyl group represented by R in Compound (I) of the present invention includes an alkanoyl group having 1 to 6 carbon atoms, for example, formyl, acetyl, propionyl, butyryl, pentanoyl and hexanoyl. The substituent includes hydroxyl, halogen such as chlorine and bromine, etc. The arylcarbonyl group represented by R includes benzoyl, α-naphthoyl, β-naphthoyl, etc. The substituent on the aryl ring includes hydroxyl, halogen such as chlorine and bromine, etc.

The following compounds are specific examples of Compound (I).

[1] DC-86-Y

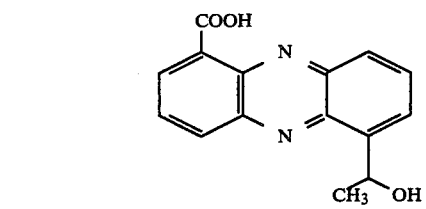

(1) Melting point: 223° to 225° C.

(2) Elemental analysis: as C$_{15}$H$_{12}$O$_3$N$_2$ Calcd. C: 67.15%, H: 4.51%, N: 10.44%. Found C: 67.03%, H: 4.62%, N: 10.50%.

Figure 1:
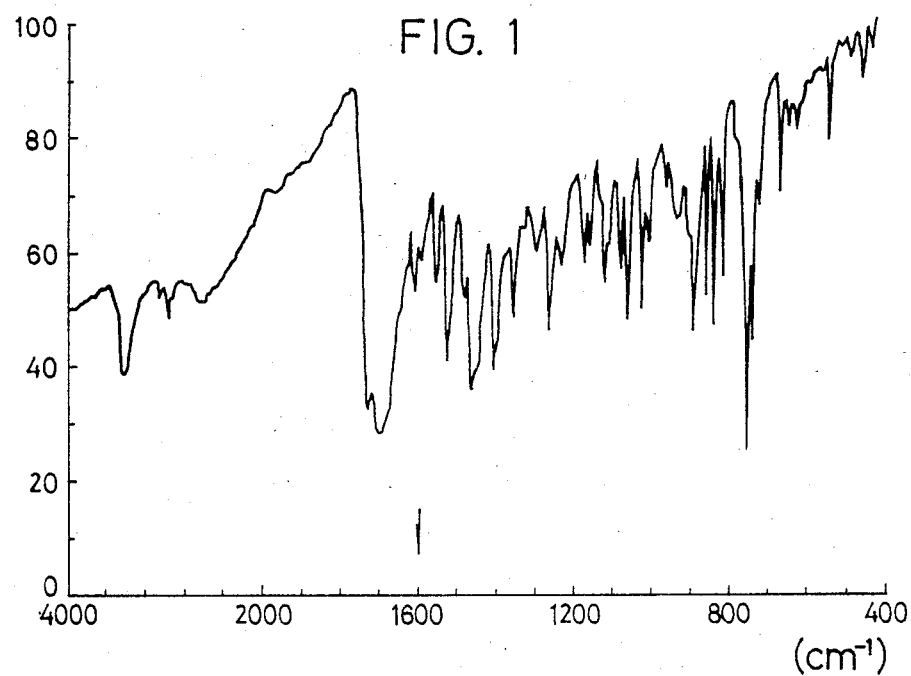
FIG. 1 shows infrared absorption spectrum of DC-86-Y.

(3) Infrared absorption spectrum (KBr tablet method): FIG. 1.

Figure 2:
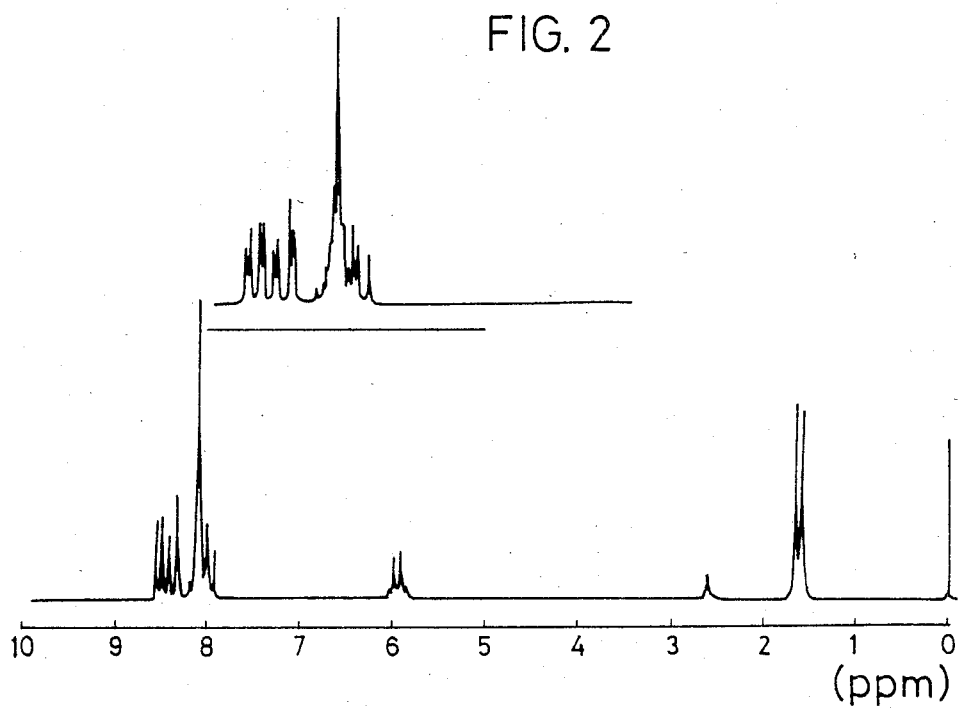
FIG. 2 shows PMR spectrum of DC-86-Y.

(4) PMR spectrum (in DMSO-d$_6$, TMS as standard): FIG. 2.

(5) CMR spectrum (in DMSO-d$_6$, TMS as standard): 165.5, 145.9, 141.0, 140.4, 139.6, 138.6, 134.7, 133.9, 132.8, 129.9, 126.7, 126.1, 126.1, 63.4, 25.4 (ppm).

(6) Specific rotation: $[\alpha]_D^{25} = +55.8°$ (C=1.0, DMSO).

(7) UV absorption spectrum (in MeOH): 253, 367 (nm).

[2] DC-86-M

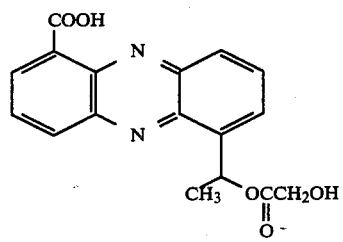

(1) Melting point: 185° to 187° C.

(2) Elemental analysis: as C$_{17}$H$_{14}$O$_5$N$_2$ Calcd. C: 62.57%, H: 4.32%, N: 8.59%. Found C: 62.42%, H: 4.15%, N: 8.60%.

Figure 3:
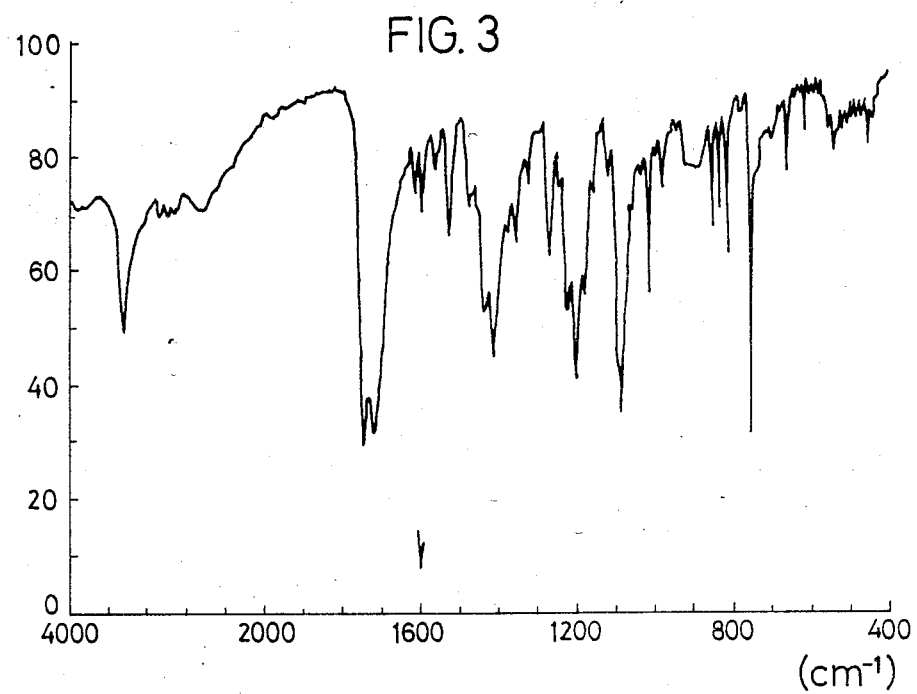
FIG. 3 shows infrared absorption spectrum of DC-86-M.

(3) Infrared absorption spectrum (KBr tablet method): FIG. 3.

Figure 4:
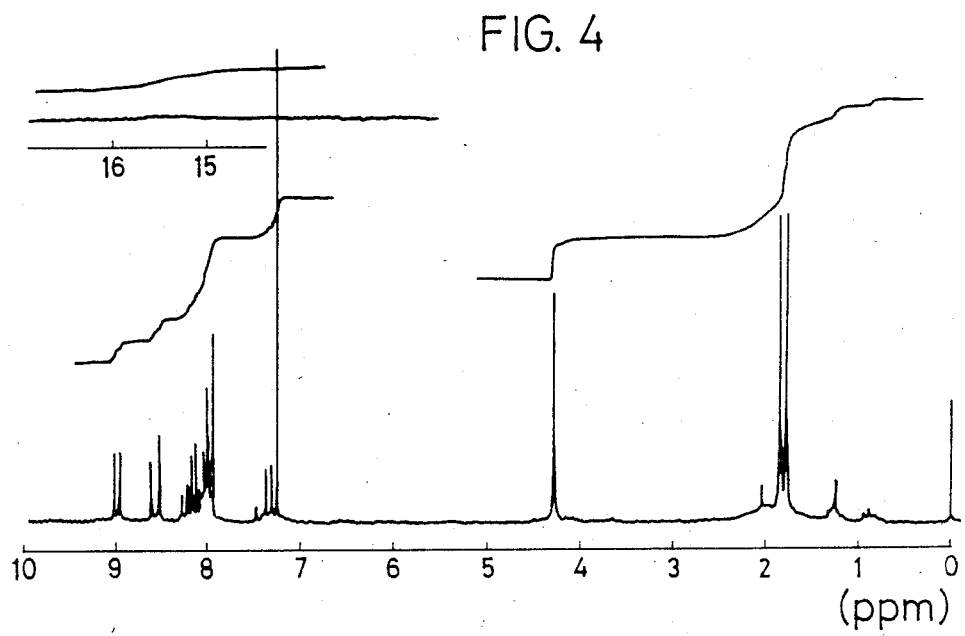
FIG. 4 shows PMR spectrum of DC-86-M.

(4) PMR spectrum (in CDCl$_3$, TMS as standard): FIG. 4.

(5) Specific rotation: $[\alpha]_D^{23} = -43.8°$ (C=0.5, CHCl$_3$).

(6) UV absorption spectrum (in MeOH): 251, 363 (nm).

[3] DC-86-R

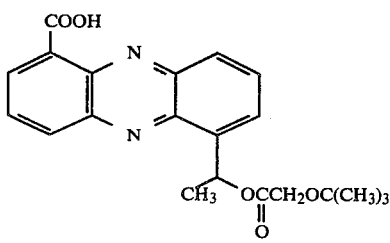

(1) Melting point: 189° to 192° C.

(2) Elemental analysis: as $C_{21}H_{22}O_5M_2$ Calcd. C: 65.95%, H: 5.80%, N: 7.33%. Found C: 65.99%, H: 5.71%, N: 7.42%.

Figure 5:
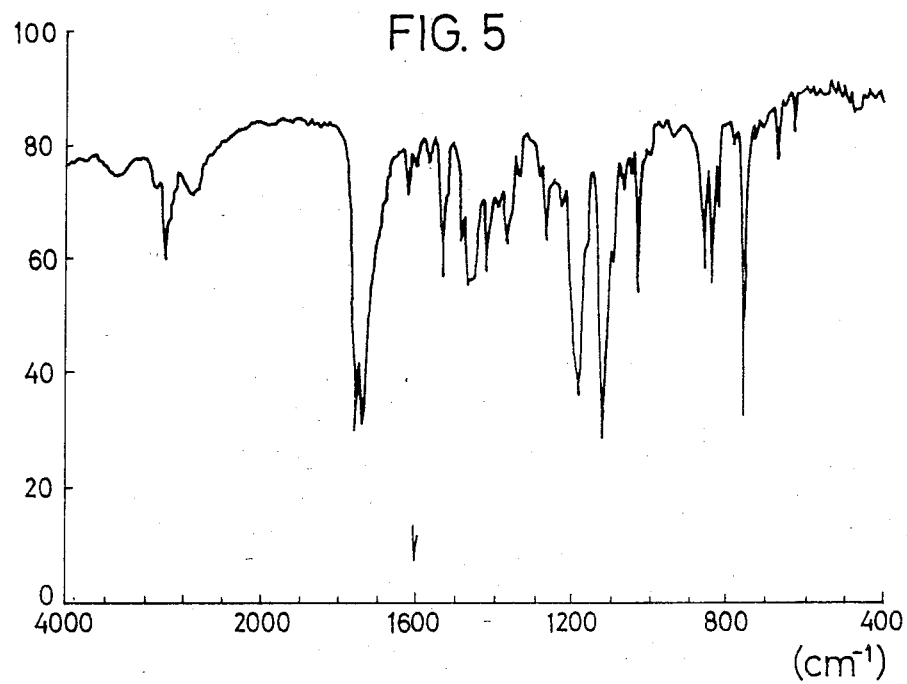
FIG. 5 shows infrared absorption spectrum of DC-86-R.

(3) Infrared absorption spectrum (KBr tablet method): FIG. 5.

Figure 6:
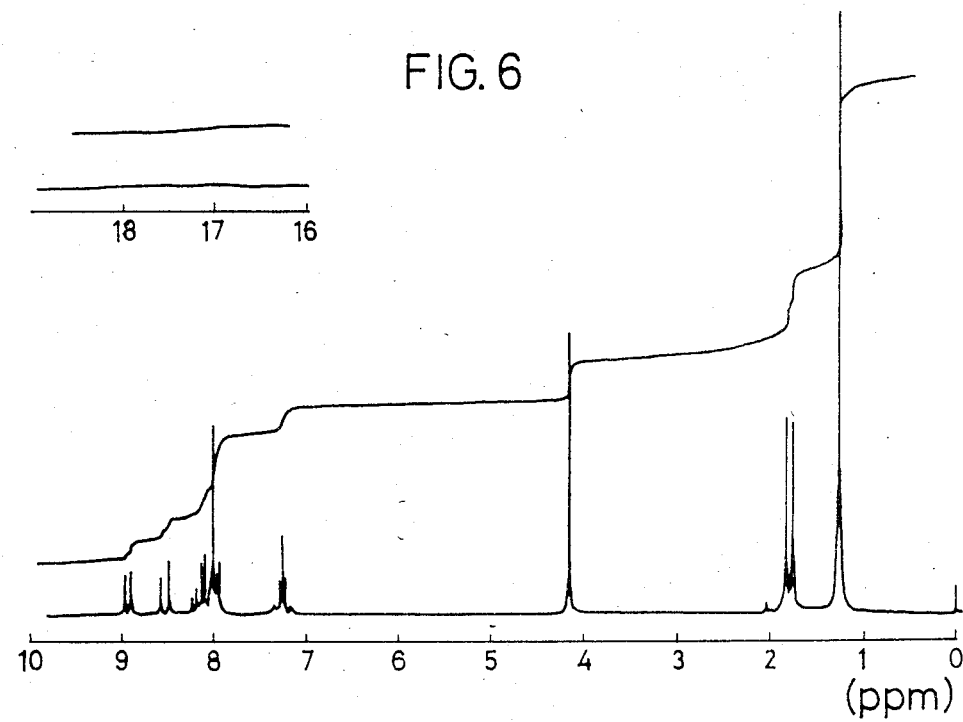
FIG. 6 shows PMR spectrum of DC-86-R.

(4) PMR spectrum (in $CDCl_3$, TMS as standard): FIG. 6.

(5) Specific rotation: $[\alpha]_D^{23} = -34.6°$ (C=0.5, $CHCl_3$).

(6) UV absorption spectrum (in MeOH): 252, 364 (nm).

[4] DC-86-C

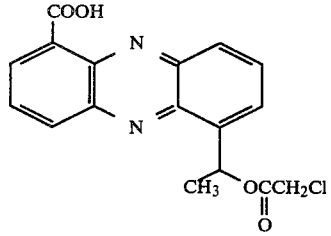

(1) Melting point: 154° to 156° C.

(2) Elemental analysis: as $C_{17}H_{13}O_4N_2Cl$ Calcd. C: 59.27%, H: 3.81%, N: 8.13%. Found C: 59.20%, H: 3.85%, N: 8.32%.

Figure 7:
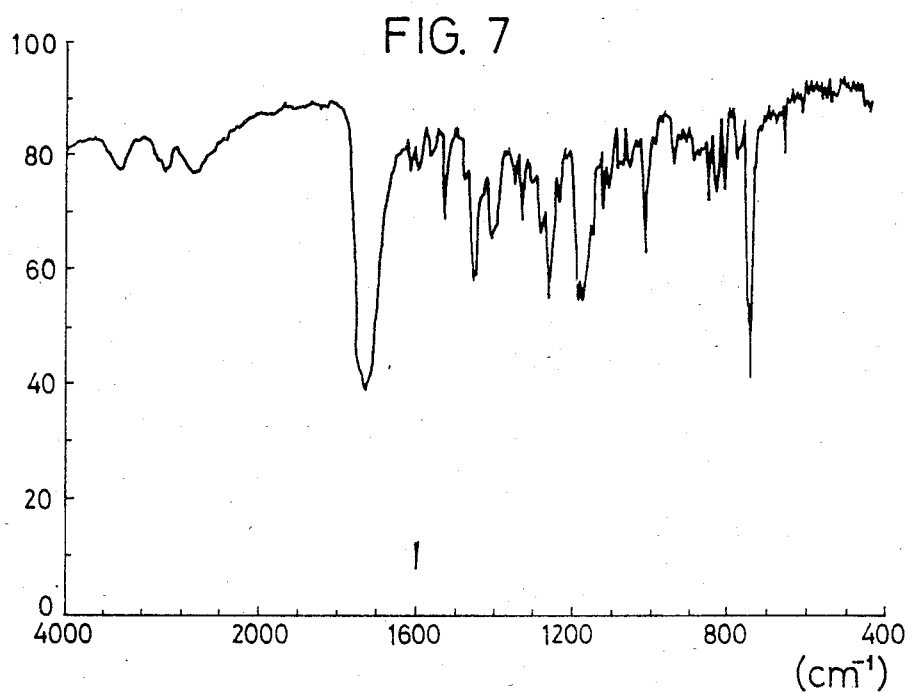
FIG. 7 shows infrared absorption spectrum of DC-86-C.

(3) Infrared absorption spectrum (KBr tablet method): FIG. 7.

Figure 8:
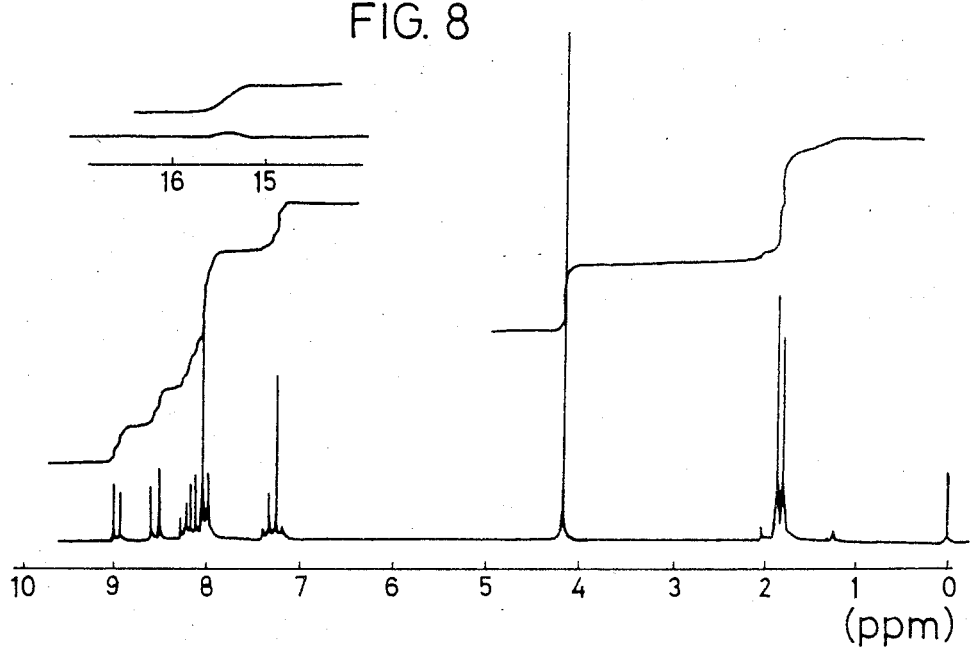
FIG. 8 shows PMR spectrum of DC-86-C.

(4) PMR spectrum (in $CDCl_3$, TMS as standard): FIG. 8.

(5) Specific rotation: $[\alpha]_D^{22} = -54°$ (C=0.6, $CHCl_3$).

(6) UV absorption spectrum (in MeOH): 254, 364 (nm).

The process for production of DC-86-Y and DC-86-M is explained below.

DC-86-Y and DC-86-M can be produced by incubating a microorganism belonging to the genus Streptomyces and having the ability to produce DC-86-Y or DC-86-M in a medium, accumulating DC-86-Y or DC-86-M in a culture medium and recovering formed DC-86-Y or DC-86-M from the culture medium.

In the process of the present invention, any microorganism can be used so long as it belongs to the genus Streptomyces and has the ability to produce DC-86-Y or DC-86-M. A preferred microorganism is DO-86 strain.

The taxonomical properties of the DO-86 strain are described below.

(A) Morphological characteristics:

Aerial mycelia are abundantly formed on ordinary media for isolation and their shape is a simple branch, flexious or spiral. Spores are in a chain of 10 or more and have smooth surface. The spores are oval (0.5 to $0.6\mu \times 1.1$ to $1.2\mu$). Formation of sporangia or sclerotia and definite septation of substrate mycelia are not observed.

The DO-86 strain was grown on various media and growth conditions, colors of the surface and the reverse of colony and soluble pigment were observed. The results are shown in Table 1.

TABLE 1

| | | Growth Conditions on Various Media | | |
| --- | --- | --- | --- | --- |
| | | Color of Colony | Growth and Color of | Soluble |
| Medium | Growth | Surface   Reverse | Aerial Mycelium | Pigment |
| Sucrose nitrate agar | good raised | light wheat to bamboo (2 ea to 2 gc) | good white to light beige (a to 3 ec) | none |
| Glucose asparagine agar | good raised | light ivory to bamboo (2 ca to 2 gc) | good white to oatmeal (a to 2 ec) | none |
| Glycerine asparagine agar | good raised | covert tan to beige (2 ge to 3 ge) | good natural string to silver gray (2 dc to 3 fe) | none |
| Starch inorganic salt agar | good flat | camel to bamboo (3 ie to 2 gc) | good white to silver gray (a to 3 fe) | none |
| Tyrosine agar | good crinkled | natural string to sepia brown (2 dc to 3 pn) | good white to light wheat (a to 2 ea) | sepia brown (3 pn) |
| Nutrient agar | good raised | white to bamboo (a to 2 gc) | none | none |
| Yeast maltose agar | good flat | camel to topaz (3 ie to 3 ne) | good white to beige gray (a to 3 ih) | cinnamon brown (3 lg) |
| Oatmeal agar | good raised | light olive drab to mustard brown (1½ li to 2 ni) | good white to natural (a to 2 dc) | mustard brown (2 pi) |
| Peptone yeast iron agar | normal flat | light olive gray (1½ ge) | none | sepia brown (3 pn) |

The color indications are given according to the classification of color by Color Harmony Manual (Container Corporation of America).

(B) Physiological characteristics:

Physiological characteristics of the DO-86 strain are shown below.

Items other than temperature and actions upon milk and cellulose show the results observed after culturing at 27° C. for 2 weeks; temperature is determined after culturing for 5 days and the actions upon milk and cellulose are observed after culturing at 27° C. for 1 month.

| 1 | Utilization of Carbon Sources | |
|---|---|---|
| | Carbon Source | Utilization |
| | L-Arabinose | ++ |
| | D-Xylose | +++ |
| | D-Glucose | +++ |
| | D-Fructose | ++ |
| | Sucrose | ++ |
| | Inositol | +++ |
| | L-Rhamnose | ++ |
| | Raffinose | +++ |
| | D-Mannitol | +++ |
| 2 | Liquefaction of gelatin | − |
| 3 | Action upon milk | peptonization + |
| 4 | Decomposition of cellulose | slightly positive |
| 5 | Hydrolysis of starch | positive |
| 6 | Optimum growth pH | 6.8–7.5 |
| 7 | Optimum growth temperature | 28–38° C. |
| 8 | Formation of tyrosinase | + |
| 9 | Formation of melanoid pigment | + |

Further, meso-diaminopimelic acid was detected in cell walls of the strain.

From the above properties, the DO-86 strain can be classified as actinomycetes belonging to the genus Streptomyces and has been named Streptomyces sp. DO-86.

This bacterium was deposited on Sept. 29, 1982 with the Fermentation Research Institute, Agency of Industrial Science & Technology, located at 1-1-3, Higashi, Yatabe-machi, Tsukuba-gun, Ibaraki-ken, Japan under the accession number FERM BP-192.

The present strain may be mutated by artificial mutation means such as ultraviolet irradiation, X-ray, irradiation and treatment with chemicals, as is the case with known bacteria belonging to the genus Streptomyces. Such a mutant can also be employed if it is capable of producing DC-86-Y or DC-86-M.

A method for incubation is described below.

For the incubation of the present invention, a conventional method for incubation of actinomycetes is generally employed. Either a natural medium or a synthetic medium can be used so long as it properly contains carbon source(s), nitrogen source(s), inorganic materials and other nutrients as the nutrients for incubation. As the carbon source, glucose, starch, dextrin, mannose, fructose, sucrose, lactose, xylose, arabinose, mannitol, molasses, etc. are employed singly or in combination. Further, depending upon the assimilability of the bacteria, hydrocarbons, alcohols, organic acids, etc. can also be employed. As the inorganic and organic nitrogen sources, ammonium chloride, ammonium sulfate, ammonium nitrate, sodium nitrate, urea, natural nitrogen-containing substances such as peptone, meat extract, yeast extract, dry yeast, corn steep liquor, soybean meal and casamino acid, and the like are employed singly or in combination. In addition, inorganic salts such as sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate, copper sulfate, etc. can be added, if necessary. Further, trace components for promoting the growth of the bacteria used or the production of DC-86-Y or DC-86-M such as vitamin $B_1$, biotin, etc. can be appropriately incorporated.

As the incubation method, a liquid culturing method, particularly a submerged stirring culture method is most suitable. The incubation is carried out at a temperature of 25° to 40° C., preferably 28° to 38° C. and at a pH of 4 to 10, preferably 6 to 8, by adding aqueous ammonia, an ammonium carbonate solution, etc. After the incubation by liquid culturing method normally for 1 to 7 days, the desired product is formed and accumulated both in the culture liquor and in the cells.

The product in the culture liquor is recovered in a similar manner to a conventional method for recovering microbial metabolites from the culture medium. The filtrate is extracted with a solvent, e.g., ethyl acetate, and the extract is concentrated, followed by purify cation by silica gel chromatography to obtain the product.

By repeating further extraction, various chromatographies, recrystallization, etc., the product having high purity can be obtained.

The compounds of general formula (I) wherein R is not a hydrogen atom, namely compounds represented by general formula (I-b):

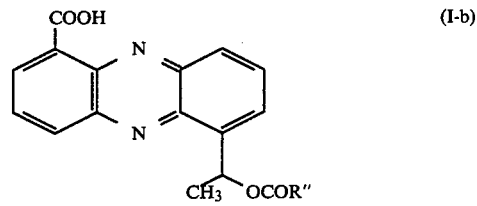

wherein R"CO is equal to R excluding a hydrogen atom, that is, R" represents unsubstituted or substituted alkyl or unsubstituted or substituted aryl, can be obtained by reacting DC-86-Y with compounds represented by general formula (II):

(wherein Z is hydroxyl or a halogen atom, e.g., a chlorine atom, a bromine atom and a fluorine atom) or reactive derivatives thereof.

The reaction is carried out in an appropriate solvent, for example, chloroform, tetrahydrofuran, benzene and methylene chloride at a temperature of 0° to 50° C. The starting compounds are employed generally in an equimolar amount at a concentration of 0.01 to 1 mol/l, and a condensing agent, e.g., DCC, is employed at a concentration of 0.01 to 0.5 mol/l.

DC-86-M can be obtained by (1) starting DC-86-R in trifluoroacetic acid as a solvent at 0° to 20° C., (2) stirring DC-86-R in 25% hydrogen bromide-acetic acid as a solvent for 20 to 30 minutes, (3) heating DC-86-R in a mixture of conc. hydrochloric acid and dioxane (1:2 v/v) under reflux; or (4) adding trimethylsylyl iodide $(CH_3)_3SiI$ to DC-86-R in chloroform or carbon tetrachloride as a solvent and allowing the mixture to react at 25° C. for 10 minutes.

Antibacterial activities of DC-86-Y, -M, -R and -C against various bacteria determined by agar dilution method (pH 7.0) are shown in Table 2.

TABLE 2

| Tested Bacteria | Minimum Inhibitory Concentration (μg/ml) | | | |
| --- | --- | --- | --- | --- |
| | DC-86-Y | DC-86-M | DC-86-R | DC-86-C |
| Staphylococcus aureus ATCC 6538P | >100 | 0.3 | 3 | 0.2 |
| Bacillus subtilis No. 10707 | >100 | 0.1 | 0.7 | 0.01 |
| Klebsiella pneumoniae ATCC 10031 | >100 | 100 | >100 | >100 |
| Escherichia coli ATCC 26 | >100 | 100 | >100 | >100 |
| Shigella sonnei ATCC 9290 | >100 | 10 | >100 | 10 |
| Salmonella typhosa ATCC 9992 | >100 | 10 | >100 | 10 |

Acute toxicities ($LD_{50}$) of DC-86-Y, -M, -R and C are 300 mg/kg, 20 mg/kg, 250 mg/kg and 40 mg/kg, respectively, in intraperitoneal administration to mice.

Anti-tumor activities of these compounds are shown below.

EXPERIMENT $5 \times 10^6$ Sarcoma 180 ascites tumor cells were transplanted to the hypoderm of the armpit cavity of ddy male mice weighing about 20 g, one group being 6 mice. 24 hours after the transplantation, 0.2 ml of a phosphate buffer saline (PBS) solution of a test compound having various concentrations was intraperitoneally administered once. The composition of PBS is 0.8 g/dl NaCl, 0.02 g/dl KCl, 1.15 g/dl $Na_2HPO_4$ and 0.02 g/dl $KH_2PO_4$ (pH 7.2). For comparison, 0.2 ml of PBS containing mitomycin C was intraperitoneally administered 24 hours after the transplantation of the tumor cells. Average tumor volume ($mm^3$) and T/C (T: average tumor volume of mice treated with the test compound, C: average tumor volume of mice treated with 0.2 ml of PBS intraperitoneally) were measured 7 days after the transplantation and the results shown in Table 3 were obtained.

TABLE 3

| Compound | Dose (mg/kg) | T/C |
| --- | --- | --- |
| DC-86-R | 200 | 0.86 |
| | 100 | 0.87 |
| | 50 | 1.06 |
| DC-86-C | 50 | dead |
| | 25 | 0.72 |
| | 12.5 | 0.98 |
| DC-86-M | 20 | 0.36 |
| | 10 | 0.82 |
| | 5 | 0.97 |
| Mitomycin C | 6 | 0.28 |

The compounds of the present invention are used as medicines based on antibacterial or anti-tumor activities. The compounds may be employed as they are or as an oral or parenteral composition (for example, as an injectable composition) in combination with pharmaceutically acceptable carriers.

As the carriers, known vehicles, surface active agents, disintegrators, liquids, etc. are employed.

The dose varies depending upon the compound and is in the range of 0.1 to 20 mg/week.

Certain specific embodiments of the present invention are illustrated by the following examples. In the examples, the substances were monitored by bioassay using Bacillus subtilis No. 10707 or under UV irradiation of 2536 angstrom using TLC plate (Merck. Art 5715).

EXAMPLE 1

As a seed strain, Streptomyces sp. DO-86 is used. The strain is inoculated in 300 ml of a seed medium (10 g/l glucose, 10 g/l soluble starch, 3 g/l beaf extract, 5 g/l yeast extract, 2 g/l bactotrypton and 2 g/l $CaCO_3$, pH 7.2) in a 2 l-Erlenmeyer flask. Culturing is carried out with shaking (220 rpm) at 30° C. for 48 hours. The resulting seed culture liquor is added to a fermentation medium having the composition described below in a 30 l-jar fermenter in the proportion of 5% (volume) to make up the medium to 15 l. Culturing is carried out at 30° C. with aeration (15 l/min) and stirring (250 rpm).

Composition of the fermentation medium: 20 g/l lactose, 10 g/l glucose, 15 g/l fermamedia, 10 g/l meat extract, 5 g/l yeast extract and 2 g/l $CaCO_3$, pH adjusted to 7.2 with NaOH (prior to sterilization).

The pH of the medium is not adjusted during the culturing and the culturing is continued for 72 hours. The cells and precipitate are separated from the culture liquor by filtration to obtain 13 l of the filtrate.

The filtrate is adjusted to pH 2.0 with conc. hydrochloric acid and extracted with 10 l of ethyl acetate. The solvent layer is taken and again extracted with 10 l of ethyl acetate. The solvent layers are combined and washed with 10 l of water. After drying over $Na_2SO_4$, the layers are concentrated to dryness, subjected to silica gel chromatography and eluted with chloroform. The fractions containing DC-86-Y and DC-86-M are collected. After the solvent is removed by distillation, the residue is recrystallized from ethyl acetate to obtain 870 mg of yellow needle crystals of DC-86-Y. Mother liquor of the recrystallization is concentrated and again subjected to silica gel chromatography, followed by elution with chloroform. From the initial fraction, DC-86-Y is obtained. The fraction is concentrated and then recrystallized from ethyl acetate to obtain 30 mg of yellow needle crystals of DC-86-Y. From the following fraction, DC-86-M is obtained. The fraction is concentrated and then recrystallized from ethyl acetate-n-hexane to obtain 30 mg of DC-86-M as yellow granules.

EXAMPLE 2

In this example, 536 mg of DC-86-Y and 396 mg of t-butoxyacetic acid are dissolved in 15 ml of anhydrous pyridine, and 618 mg of dicyclohexylcarbodiimide is added to the solution at room temperature while stirring. Stirring is continued for 3 hours and the reaction mixture is poured into ice water. The mixture is then adjusted to pH 5.0 with 2N-hydrochloric acid and extracted three times with 100 ml each of ethyl acetate. The ethyl acetate layer is washed with water, dried over $Na_2SO_4$, and concentrated under reduced pressure. 20 ml of ethyl acetate is added thereto and insoluble matters are removed. The filtrate is concentrated, subjected to silica gel chromatography, and eluted with chloroform.

The fractions containing DC-86-R are concentrated under reduced pressure and recrystallized from benzene-n-hexane to obtain 500 mg of DC-86-R as light yellow needles.

EXAMPLE 3

In this example, 80 mg of DC-86-R is dissolved in 5 ml of trifluoroacetic acid and the solution is stirred at room temperature for 20 minutes. Trifluoroacetic acid is distilled off under reduced pressure and the residue is recrystallized from ethyl acetate-n-hexane to obtain 45 mg of DC-86-M as yellow granules.

EXAMPLE 4

In this example, 200 mg of DC-86-Y and 140 mg of monochloroacetic acid are dissolved in 5 ml of anhydrous pyridine, and 260 mg of dicyclohexylcarbodiimide is added to the solution at room temperature while stirring. Stirring is continued for 35 minutes at room temperature. The reaction mixture is poured into ice water and the pH is adjusted to 5.0 with 6N-hydrochloric acid, followed by extraction with chloroform. The chloroform layer is washed with water, dried over $Na_2SO_4$, and concentrated under reduced pressure. 15 ml of ethyl acetate is added thereto and insoluble matters are removed. The filtrate is concentrated, subjected to silica gel chromatography and eluted with chloroform. The fractions containing DC-86-C are concentrated under reduced pressure and recrystallized from benzene-n-hexane to obtain 190 mg of DC-86-C as yellow granular crystals.

What is claimed is:

1. A phenazine compound represented by the formula:

[Chemical structure: phenazine with COOH and CH(CH₃)(OR) substituents]

wherein R represents an unsubstituted or substituted lower alkanoyl group; the substituent of the lower alkanoyl group being a member selected from the group consisting of a hydroxyl group, a halogen atom and t-butoxy.

2. A phenazine compound according to claim 1 wherein the substituent of the lower alkanoyl group is a hydroxyl group.

3. A phenazine compound according to claim 1, wherein the substituent of the lower akanoyl group is a halogen atom.

4. A phenazine compound according to claim 1, wherein the substituent of the lower alkanoyl group is t-butoxy.

5. A phenazine compound according to claim 1, wherein the alkanoyl group contains 1 to 6 carbon atoms.

* * * * *